United States Patent
Arslan et al.

(10) Patent No.: US 11,197,989 B2
(45) Date of Patent: Dec. 14, 2021

(54) CANNULA ASSEMBLY AND BLOOD PUMP ASSEMBLY AND USE THEREOF

(71) Applicant: Berlin Heart GmbH, Berlin (DE)

(72) Inventors: Nedim Arslan, Berlin (DE); Kim Peter Winterwerber, Berlin (DE); Michael Matthes, Altlandsberg (DE); Heiko Gundlach, Berlin (DE); Benjamin Daniel Kaebe, Duncraig (AU); Gerhard Lauterbach, Berlin (DE)

(73) Assignee: Berlin Heart GmbH, Berlin (DE)

( * ) Notice: Subject to any disclaimer, the term of this patent is extended or adjusted under 35 U.S.C. 154(b) by 457 days.

(21) Appl. No.: 16/091,790

(22) PCT Filed: Apr. 10, 2017

(86) PCT No.: PCT/EP2017/058567
§ 371 (c)(1),
(2) Date: Oct. 5, 2018

(87) PCT Pub. No.: WO2017/174821
PCT Pub. Date: Oct. 12, 2017

(65) Prior Publication Data
US 2019/0160212 A1    May 30, 2019

(30) Foreign Application Priority Data

Apr. 8, 2016 (EP) .................... 16164527

(51) Int. Cl.
*A61M 60/857* (2021.01)
*A61F 2/06* (2013.01)
*A61M 1/36* (2006.01)

(52) U.S. Cl.
CPC ............. *A61M 60/857* (2021.01); *A61F 2/06* (2013.01); *A61F 2220/0033* (2013.01); *A61M 1/3659* (2014.02)

(58) Field of Classification Search
CPC ............. A61M 60/857; A61M 1/3659; A61M 60/00; A61M 1/00; A61M 39/10; A61F 2/06; A61F 2220/0033; A61D 1/025
See application file for complete search history.

(56) References Cited

U.S. PATENT DOCUMENTS 6,186,999 B1    2/2001 Chen
7,258,679 B2 *  8/2007 Moore ................ A61M 60/857
                                                604/164.11
(Continued)

FOREIGN PATENT DOCUMENTS

CA    2391234 A1    5/2000
CN    1662766 A     8/2005
(Continued)

OTHER PUBLICATIONS

International Search Report with English translation, issued in International Application No. PCT/EP2017/058567, dated Dec. 7, 2017, pp. 1-3, European Patent Office, Rijswijk, Netherlands.
(Continued)

*Primary Examiner* — Shirley X Jian
(74) *Attorney, Agent, or Firm* — Crowell & Moring LLP (57) ABSTRACT

A cannula assembly is provided, the cannula assembly comprising a cannula, in particular a graft, for forming a flow channel for bodily fluids, in particular for blood, and a protective element for the cannula, wherein the protective element defines a channel for the cannula, wherein the cannula runs through the channel of the protective element at least in sections, wherein the protective element comprises a plurality of segments, wherein the segments are arranged next to one another in a sequence and wherein each segment defines a sub-section of the channel of the protec- (Continued)

tive element. A blood pump assembly and a method for using the cannula assembly and the blood pump assembly are also provided.

26 Claims, 9 Drawing Sheets

(56) References Cited

U.S. PATENT DOCUMENTS

| | | | |
|---|---|---|---|
| 7,303,553 B2 * | 12/2007 | Ott | A61M 60/00 |
| | | | 604/533 |
| D865,954 S * | 11/2019 | Mottola | D24/129 |
| 2004/0087986 A1 | 5/2004 | Ott | |
| 2006/0167333 A1 | 7/2006 | Moore et al. | |
| 2013/0060268 A1 | 3/2013 | Herrig | |
| 2015/0290370 A1 | 10/2015 | Crunkleton et al. | |

FOREIGN PATENT DOCUMENTS

| | | |
|---|---|---|
| CN | 1961237 A | 5/2007 |
| CN | 201504076 U | 6/2010 |
| WO | 2004/001272 A1 | 12/2003 |

OTHER PUBLICATIONS

Chinese Office Action with English translation, dated Sep. 30, 2020, pp. 1-22, Chinese Patent Application No. 201780033007.5, China National Intellectual Property Administration, Beijing, China.

* cited by examiner

CANNULA ASSEMBLY AND BLOOD PUMP ASSEMBLY AND USE THEREOF

CROSS-REFERENCE TO RELATED APPLICATIONS

This application is a 371 nationalization of international patent application PCT/EP2017/058567 filed Apr. 10, 2017, which claims priority under 35 USC § 119 to European patent application 16 164 527.0 filed Apr. 8, 2016. The entire contents of each of the above-identified applications are hereby incorporated by reference.

TECHNICAL FIELD

The invention lies in the field of medical technology and relates to a cannula assembly and a blood pump assembly and use thereof.

DETAILED DESCRIPTION

In the present context, a cannula is understood to mean a conduit element suitable for forming a flow channel for a bodily fluid, for example blood.

Implantable cannulas which can be embedded temporarily or permanently in the bodily tissue of a patient are of particular interest. To this end, the cannulas are generally made of a biocompatible material wholly or at least partially, in particular on their surfaces. An example of an implantable cannula is a graft, which generally has a textile carrier structure. This can be sealed already prior to its use by means of a sealing material, such as beef gelatine, or can be sealed only once impregnated with blood (what is known as glotting). Grafts, for example, are used as vascular prostheses, wherein they are connected at one end to a blood vessel or the heart of the patient, for example by direct sewing or by means of a sewing ring, and are connected for example directly or indirectly at the other end to a further conduit element and/or an implanted or external blood pump.

Implantable cannulas, in particular grafts, are typically very flexible and easily deformable. These absolutely desired properties of grafts and comparably flexible cannulas can sometimes also lead to problems, in particular in respect of their implantation. For example, there is the risk that the cannula will become kinked or compressed. In addition, there is the risk that the cannula will become damaged, for example by means of a scalpel or another instrument, during the implantation or during a subsequent surgical intervention.

It is therefore that object to solve the above-described problems fully or at least partially and also to simplify the handling of a cannula to the greatest possible extent. An improved cannula assembly should thus offer maximum mechanical protection for a cannula of the cannula assembly. In addition, an improved cannula assembly should be characterised by maximum ease of use, in particular before or during implantation. A blood pump assembly improved accordingly and a method improved accordingly for use of the cannula assembly and of the blood pump assembly are also desirable.

A cannula assembly of the type proposed here therefore comprises a cannula of the type described at the outset for forming a flow channel for bodily fluids, in particular for blood. If the cannula is a graft, the cannula typically comprises a textile carrier structure, which for example can be embodied in the form of a tube or corrugated tube. The textile carrier structure is for example formed from fibres. In particular, potential fibres are plastic fibres, such as polyester fibres. The fibres of the carrier structure for example can be woven or knitted. The carrier structure can be sealed, and therefore made impermeable for the fluid that is to be conveyed, using sealing material, for example using gelatine, such as beef gelatine. The cannula can have connection elements at one or both of its ends, as has already been mentioned above and as will be described in greater detail further below.

The cannula assembly, additionally to the cannula, also comprises a protective element for the cannula, which protective element likewise can be implanted and is formed as a separate component of the cannula assembly, produced independently of the cannula. The protective element has the function of preventing or minimising, to the greatest possible extent, damage to the cannula caused by mechanical stresses acting on the cannula from outside. In particular, the protective element reduces the risk that the cannula will become kinked or compressed or will be damaged by a scalpel or another instrument. For this purpose, the protective element defines or delimits a channel for the cannula. The cannula runs fully or at least in sections through this channel. Accordingly, the flow channel delimited by the cannula also runs fully or at least in sections within the channel of the protective element. The cannula is therefore guided laterally by the channel of the protective element. The channel of the protective element will therefore also be referred to hereinafter as a guide channel. The guide channel and the flow channel of the cannula run substantially in parallel and coaxially with one another, at least in the portions in which the flow channel runs through the guide channel.

The protective element proposed here comprises a plurality of segments, i.e. for example two or more segments, preferably more than three or more than four segments, typically between 4 and 20 segments. The segments are arranged next to one another in a sequence. Each of the segments defines an axial sub-section of the channel of the protective element, wherein the sub-section passes fully through the corresponding segment. For this purpose, the segments for example are sleeve-shaped and/or each have an opening which runs fully through the particular segment in the direction of the sequence of segments and in each case forms a sub-section of the channel.

When the cannula assembly is assembled, the cannula is introduced wholly or at least partially into the channel of the protective element, typically by pulling or pushing (which presupposes sufficient stability of the cannula) the cannula into the channel or by pushing or pulling the protective element over the cannula. The guide channel is preferably sufficiently wide to enable axial displacements of the protective element relative to the cannula passing through the guide channel and axial compensation movements between the protective element and the cannula (in particular in the event of bending movements of the cannula assembly). In particular, tensile stresses acting on the cannula, which in particular in the case of sensitive grafts could lead to damage, can also be minimised hereby. For this purpose, a (minimal) diameter or a (minimal) cross-sectional area of the guide channel for example can be larger than a (maximum) outer diameter or a (maximum) outer cross-sectional area of the cannula.

Accordingly, for example a (minimal) inner diameter of the segments, that is to say the (minimal) diameter of the above-mentioned openings of the segments can be larger than a (maximum) outer diameter of the cannula. In this way, a free gap can be created between inner walls of the segments surrounding the guide channel radially (and defining the respective openings) and an outer surface of the cannula, which gap can be wholly or at least in sections in the form of an annular gap.

The segments of the protective element are connected to one another. The protective element thus forms a unit which is mechanically held together independently of the cannula or other components.

In order to improve the handling of the cannula assembly, the protective elements for example can be connected to one another in such a way that relative rotary movements of the segments relative to one another about a longitudinal axis of the channel (or of the protective element) are possible, without at the same time cancelling or damaging the connections between the segments. For example, the segments are connected to one another in such a way that segments that are next to one another in the sequence are rotatable relative to one another through at least 3° or through at least 5° about a longitudinal axis of the channel, without the connection between these segments being cancelled or damaged. It is also possible that the segments are connected to one another in such a way that segments that are next to one another in the sequence are rotatable relative to one another through 360° about a longitudinal axis of the channel, without the connection between these segments being cancelled or damaged. By means of the described rotations, it is for example also possible for an individual segment or a plurality of segments of the protective element to be rotated relative to the cannula about the longitudinal axis of the cannula. Hereinafter, various examples will be provided for connections which allow the described rotational movements between the segments.

For example, the protective element can comprise connection elements which connect the segments to one another. The connection elements for example can be connected in an integrally bonded manner to the segments, for example by means of an adhesive. For example, each of the connection elements can be connected in an integrally bonded manner to two or more than two of the segments or to each of the segments, for example by adhesive bonding of the connection element to the relevant segments. The connection elements can be components produced separately from the segments, or can be integral constituent parts of the segments or regions of the segments. Typically, the connection elements are disposed radially outside the guide channel. Examples of the connection elements will be provided further below.

The segments can be connected to one another for example in a form-fitting manner. This can be achieved for example by means of the aforesaid connection elements, which can be integrated in the segments and/or can be parts or sub-regions of the segments, as will be described in greater detail further below.

In order to make the protective element flexible and at the same time enable a simple and relatively economical design, the segments can be formed wholly or at least partially of an elastically deformable polymer. Additionally or alternatively, the connection elements can also be formed wholly or at least partially from an elastically deformable polymer. The polymer of the segments and the polymer of the connection elements can be identical or different from one another. The polymer in question can be formed by just one polymer or a mixture of a number of different polymers. For example, the segments and/or the connection elements can be formed wholly or at least partially of a silicone, a silicone elastomer, a polyurethane, or another elastically deformable plastic. For example, it is also possible however that the segments are not formed wholly or merely partially of in elastically deformable polymer, and instead for example are formed from a dimensionally stable polymer or from a metal, such as titanium. The flexibility of the protective element can be achieved in this case primarily by the connection elements, in particular if these are formed wholly or partially from a flexible material, such as the aforesaid polymer, or if they are flexible or elastically deformable on account of their form. Suitable forms are for example cable-like, wire-like or tube-like forms with sufficiently small outer diameters.

Further materials can be integrated in the elastically deformable polymer of the segments and/or the connection elements, such as metals, in particular titanium. The segments and/or the connection elements can consist wholly or partially of composite materials, wherein the particular elastically deformable polymer of the segment or of the connection element typically constitutes the matrix of the composite material in question.

The segments and/or the connection elements for example can be shaped parts. For example, the segments and/or the connection elements can be injection-moulded parts, that is to say produced by means of injection moulding. The segments can be of identical form in a mechanically unloaded state. The connection elements can also be of identical form in a mechanically unloaded state. In the case of injection-moulded parts, just one injection mould for the segments or the connection elements can thus be sufficient.

In a particular embodiment of the cannula assembly, the connection elements of the protective element comprise at least one cable-shaped element. Cable-shaped elements are understood to be elements extending along the longitudinal axis, such as cables, which extend over a number of segments. Here, the extent along the dimension of the longitudinal axis is much greater than in the remaining dimensions transverse to the longitudinal axis. Besides cable-shaped elements which have a cable-like cross section, the cable-shaped elements can also have a strip-like cross section (thus referred to here also as strip-shaped elements), i.e. the cable-shaped element can have a width transverse to the longitudinal direction much greater than its height. Here, the width can be more than 10 times the height. However, the width is shorter than the length. The strip-shaped elements in one embodiment can also be tubular elements which enshroud the segments over their entire circumference. Here, however, a high flexibility of the material of the tubular element must be ensured so that the segments can be rotated or inclined relative to one another. In some embodiments of the cable-shaped elements it is possible that each of the connection elements is provided by a cable-shaped element of this kind or that the protective element, in addition to the cable-shaped elements, also comprises other connection elements. The at least one connection element, for example in the form of a cable-shaped element, is for example directly connected to two or to more than two of the segments or to each of the segments and is directly fastened thereto, for example by adhesive bonding. The respective connection element or cable-shaped element extends in an axial direction, that is to say for example along the guide channel or along a longitudinal axis of the cannula assembly, along all segments or at least along those segments to which the connection element or cable-shaped element is directly connected. The connection element, for example in the form of a cable-shaped element, or the connection elements, for example in the form of cable-shaped elements, can be tube-like or wire-like, for example.

Connections between the segments by means of connection elements in the form of cable-shaped elements of this kind for example make it possible to connect the segments to one another in such a way that the above-described rotational movements between the segments are possible. A rotation of 360° or more, preferably of 270° or more, or of 180° or more is ruled out in some exemplary embodiments.

If two or more connection elements, for example the aforementioned cable-shaped elements, are provided, these can be arranged distanced from one another around the protective element or around the segments with respect to a (azimuthal) circumferential direction, preferably in a manner distributed uniformly over the circumference of the segments. If, for example, exactly three (or four) connection elements (for example cable-shaped elements) are provided, these are preferably arranged from one another in the circumferential direction of the segments at equal distances for example of 120° (or 90°).

The segments can have radially outwardly directed protrusions, at which the at least one connection element, for example in the form of a cable-shaped element, is supported and/or fastened (for example by gluing). The connection elements or cable-shaped elements can run wholly or at least in sections in a freely-supporting manner between the radially outwardly directed protrusions of the segments, that is to say radially distanced from the respective segments. For example, this can be achieved in that the axial extent of the protrusions is smaller than an axial extent of the segment in question. A severing of the connection element or of the cable-shaped element, for example by means of a hand-held cutting instrument, such as a scalpel, is hereby facilitated. The protrusions for example can be shaped as annular widened portions of the respective segments. For example, the protrusions can have receptacles, for example in the form of indentations, through which an axial sub-section of a connection element or cable-shaped element runs.

Additionally or alternatively to the cable-shaped elements, the protective element can also comprise connection elements which are integrated in axial end regions of the segments or are realised by the form of these end regions. These connection elements for example can be designed to produce form-fitting connections between adjacent segments. For example, each of the segments can have a first axial end region and a second axial end region, wherein the first axial end regions of the segments are formed in a manner complementary to the second axial end regions of the segments. These end regions thus constitute connection elements of the protective element or are carriers for connection elements of the protective element, such as the ribs and grooves described below. The first and the second axial end regions of segments that are next to one another in the sequence can overlap axially and can be in mutual engagement. A mechanical connection between the segments is produced as a result of this engagement. The segments are preferably elastically deformable in these axial end regions, for example because they are formed from an elastically deformable material or polymer, as described above, such that these connections can be produced and cancelled manually by axially pushing together or pulling apart segments arranged next to one another, respectively.

For example, the first axial end region of each segment can have a first rib and a first groove, wherein the first rib and the first groove are arranged on an outer side (that is to say on an outer surface) of the segment facing away from the channel (radially), wherein the second axial end region of each segment has a second rib formed in a manner complementary to the first groove, and has a second groove formed in a manner complementary to the first rib, wherein the second rib and the second groove are arranged on an inner side (that is to say an inner surface) of the segment facing the channel (radially). The first and second ribs and the first and second grooves can surround the channel (in the azimuthal direction) in each case completely or partially. The first groove and/or the second groove are/is typically furrow-shaped. For example, the first groove can be formed as a furrow on the outer side of the respective segment. Additionally or alternatively, the second groove is formed as a furrow on the inner side of the respective segment.

By means of form-fitting connections between the segments, it is in particular possible to connect the segments to one another in such a way that the above-described rotary movements between the segments are possible. In addition, form-fitting connections are embodied in such a way that they can be produced and cancelled manually by axially pushing together or pulling apart segments arranged next to one another, respectively, as has been described above with reference to a specific example.

For example, one, more or each of the segments of the protective element can have a slot which extends in the axial direction over an axial total length of the particular segment(s) and in the radial direction from an outer side (outer surface) of the respective segment(s) facing away from the channel (radially) to an inner side (inner surface) facing the channel (radially). A slot of this kind can be widened or expanded manually or by means of a suitable instrument by appropriate deformation of the respective segment(s). If the gap is widened or expanded sufficiently widely, the segment(s) in question can be removed from the cannula in a lateral, non-axial direction, provided it/they has/have first been separated from the adjacent segments.

This thus allows the removal of a slotted segment also when the cannula is already connected at both ends to further conduit elements and/or to blood vessels.

The cannula assembly typically comprises a first end, referred to hereinafter also as the rear end of the cannula assembly, which is designed for indirect or direct connection to a bodily organ or a cavity, in particular a bodily cavity, conducting a bodily fluid, and a second end, also referred to hereinafter as the front end, which is designed for connection/attachment to a conduit element (for example an outlet manifold) or a functional element of the liquid-conveying means (blood pump).

The cannula can have at least one connection element. For example, the cannula can also have a connection element at one axial end region of the cannula and, as necessary, also at a further, opposite axial end region of the cannula.

At least one connection element of the cannula can be designed to produce a connection between the cannula and a bodily blood vessel or heart of a patient. For example, a connection element of this kind can be a sewing ring.

At least one connection element of the cannula can be designed to establish a fluid-tight connection between the cannula and a further conduit element for the liquid to be conveyed, for example a connection to a pipe element inserted into the axial end region of the cannula. This pipe element for example can be a sub-section of an outlet or an outlet manifold of a blood pump or an inlet or an inlet manifold of a blood pump or also a connection cannula. A connection element of this kind can be embodied for example in the form of a clamp which surrounds the respective axial end region of the cannula. In a clamped state, the clamp can be transferred in order to exert a clamping force acting radially inwardly on the endpiece of the cannula and thus produce a fluid-tight clamping connection between the cannula and a pipe element inserted into the axial end region of the cannula. For example, the clamp for producing and/or stabilising the clamped state of the clamp can comprise a screw closure with a clamping bolt and a corresponding threaded part or a detent closure with corresponding detent elements or a resilient spring element. For example, the clamp can be manufactured from a metal and/or a polymer.

A blood pump assembly of the type proposed here preferably comprises a cannula assembly of the type proposed here and a blood pump (VAD), in particular an implantable blood pump or an external blood pump. For example, the blood pump can be an axial pump or a centrifugal pump or a pump that conveys fluid in a pulsed manner. The blood pump typically comprises an inlet and an outlet. In the case of a left-ventricular blood pump assembly, it can be provided for example that the inlet of the blood pump is connected directly or indirectly to a left ventricle, for example via an inlet manifold. The outlet of the blood pump can be connected directly or indirectly, for example via an outlet manifold, to the front end of the cannula assembly. The cannula of the cannula assembly can be connected via the rear end to a blood vessel of the patient, for example to the aorta or the aortic arch.

The cannula assembly can have a connector at the front end of the cannula assembly. For example, the connector can be fastened to the protective element, for example to a foremost segment of the protective element. The blood pump can have a connection part corresponding to the connector for producing a releasable connection between the cannula assembly and the blood pump. For example, the connector can be a snap-action connector having at least one flexible snap-action element. For example, the connector can comprise a claw ring, for example a claw ring having claws of the type described in publication WO 2004/001272 A1. For example, the claw ring can be arranged rotatably and/or displaceably on a foremost end of the protective element, for example on the foremost segment of the protective element.

The corresponding connection part for example can have at least one holding surface corresponding to the at least one flexible snap-action element for producing a releasable latched connection between the at least one holding surface and the at least one snap-action element. For example, the connection element can comprise a detent ring having detent ring holding surfaces, for example a detent ring of the type described in publication WO 2004/001272 A1. The detent ring for example can be integrated in the connection part and for example can be embodied as an axial end region of the connection part.

The connection part of the blood pump corresponding to the connector of the cannula assembly can comprise an adapter element or can be embodied as an adapter element. The adapter element can be fixedly connected to a conduit element of the blood pump, for example an outlet or an outlet manifold of the blood pump, for example by means of an adhesive, such as a silicone adhesive. The adapter element can in some exemplary embodiments can be manufactured partially or wholly from a metal material, for example from titanium. The aforesaid conduit element can also be manufactured from a metal material, such as titanium, or from a polymer, such as a silicone.

The adapter element can have a sleeve-shaped region which surrounds an axial end region of the conduit element of the blood pump completely or partially. For example, the above-mentioned detent ring can axially border the sleeve-shaped region. The sleeve-shaped region can have substantially radially extending openings. Proceeding from the conduit element, fastening elements can then run through the openings and connect the adapter element to the conduit element. For example, the fastening elements are adhesively bonded to the conduit element by means of an adhesive, for example silicone adhesive. The fastening elements can be formed completely from the adhesive. In particular, foot ends of the fastening elements can be connected to the conduit element in an integrally bonded manner, wherein head ends of the fastening elements can protrude from the openings, preferably both radially outwardly and laterally beyond outer edges of the openings. The head ends can be wider than the openings, such that the fastening elements cause a form-fitting connection between the conduit element and adapter element, similarly to a rivet connection.

With use of a cannula assembly or a blood pump assembly of the kind proposed here, the protective element for example is shortened. This can be performed for example before or during implantation of the cannula assembly or the blood pump assembly. Here, two segments of the protective element arranged next to one another in the sequence are separated from one another. This can be achieved for example by severing at least one, precisely one, or each connection element of the protective element connecting the two adjacent segments to one another, moreover by means of a manually guided cutting instrument, for example by means of a scalpel. This can be performed particularly easily in particular in the case of the cable-shaped connection elements. Additionally or alternatively, depending on the embodiment of the connection elements, the two segments arranged next to one another can also be separated by being manually pulled apart from one another, for example until a mutual engagement existing between connection elements connecting the two segments arranged next to one another has been cancelled by pulling said segments away from one another. This is possible in particular if the connection elements, as described above, are embodied as axial end regions of the segments shaped in a complementary manner.

In principle, the cannula assembly described here, instead of the protective element proposed here, can also have an alternative protective element for the cannula, which protective element forms a guide channel for the cannula, in which the cannula runs wholly or at least in sections, and which for example can be embodied in the form of a flexible tube. For example, the connection element described here of the cannula (for example in the form of the clamp) can also be provided in a cannula assembly having an alternative protective element of this kind. Accordingly, the blood pump assembly described here can also be realised in principle with this alternative cannula assembly. The alternative protective element can then be connected to the connector in the same way as the protective element proposed here.

The cannula assembly is typically fully implantable. To this end, besides the cannula, in particular also the protective element and all other components of the cannula assembly can consist wholly or at least partially, in particular on their surfaces, of biocompatible materials.

Figure 1:
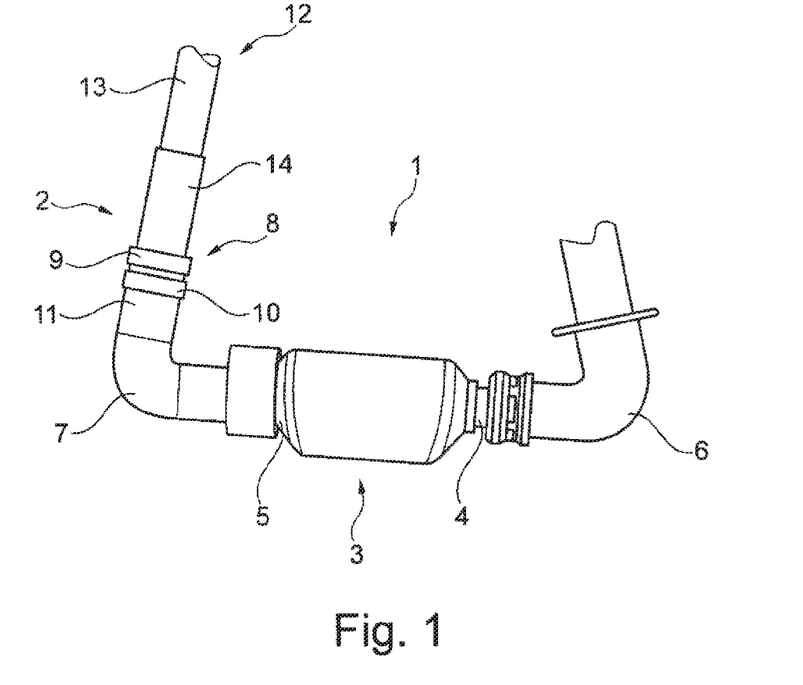
FIG. 1 shows a side view of an example of a blood pump assembly with a cannula assembly of the type proposed here.
Figure 2:
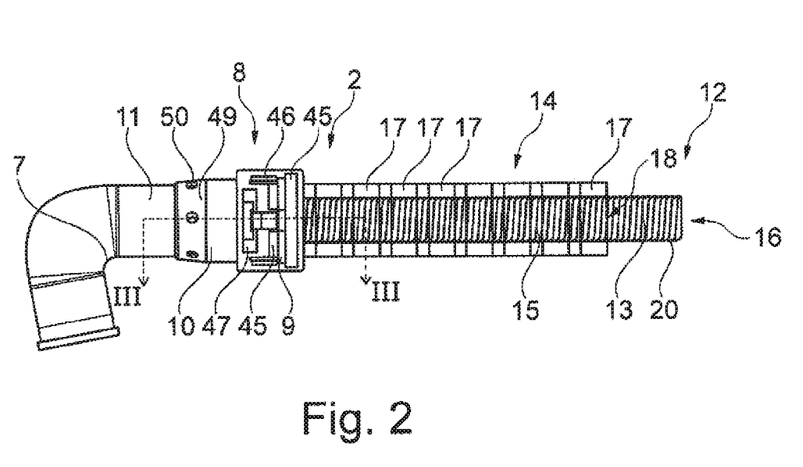
FIG. 2 shows a side view of the cannula assembly shown in FIG. 1.
Figure 3:
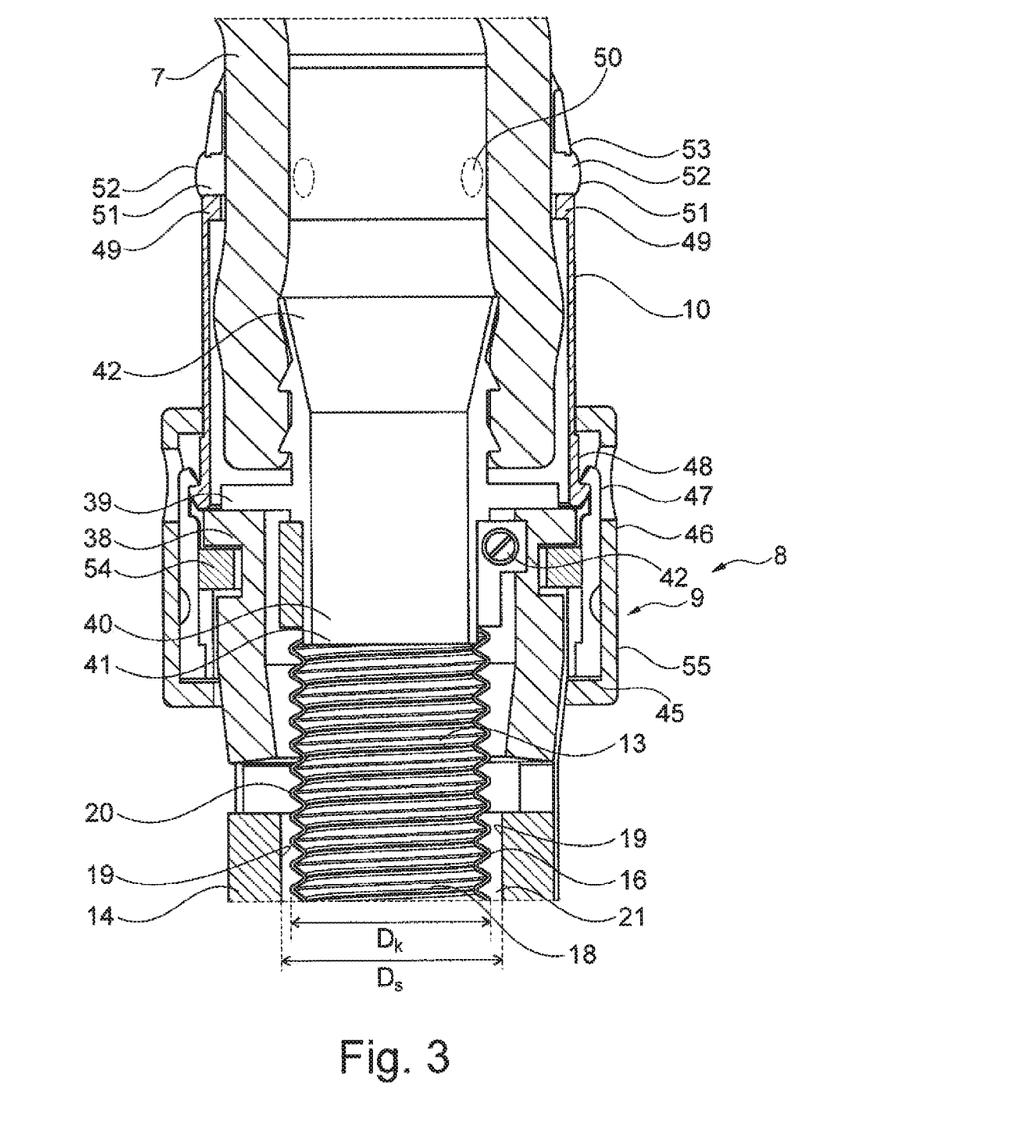
FIG. 3 shows a sectional illustration of the cannula assembly shown in FIG. 2 in accordance with the longitudinal section marked in FIG. 2 and denoted by the numeral III.
Figure 4A:
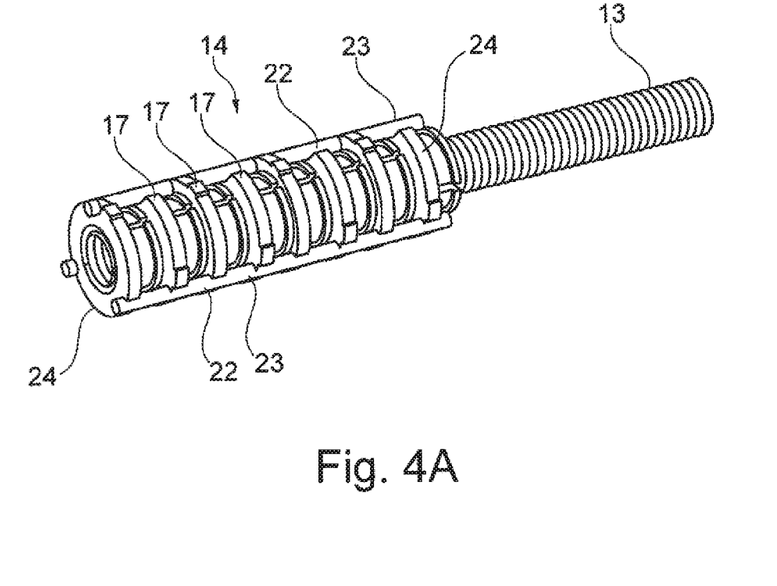
FIG. 4A shows perspective views of an example of a protective element of the cannula assembly shown in FIGS. 1 to 3.
Figure 4B:
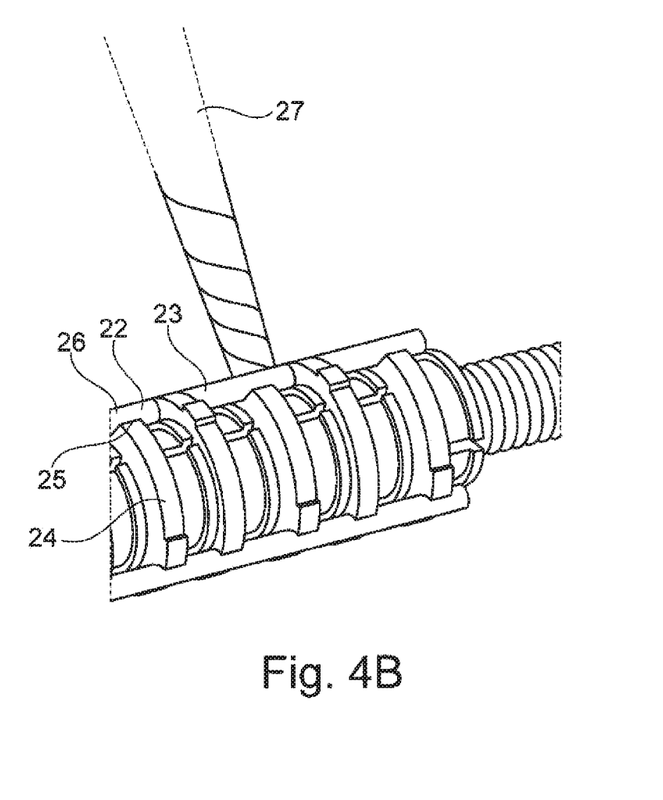
FIG. 4B shows perspective views of an example of a protective element of the cannula assembly shown in FIGS. 1 to 3.
Figure 4C:
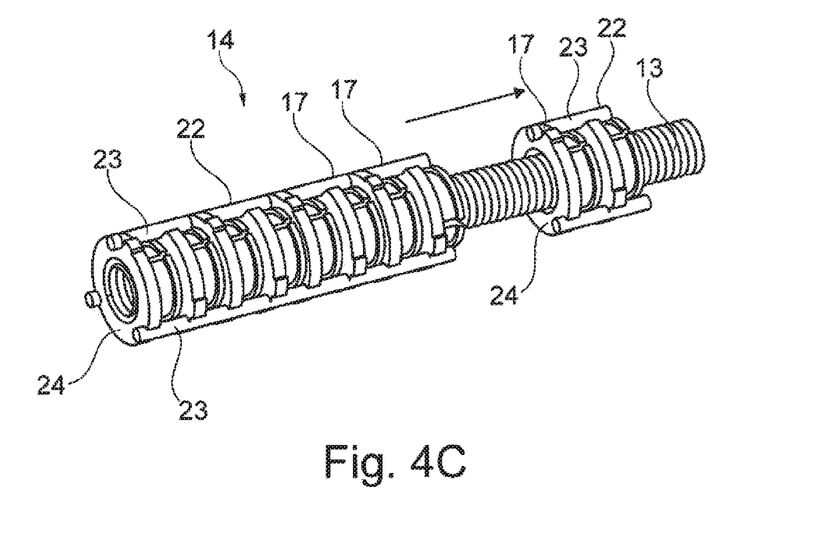
FIG. 4C shows perspective views of an example of a protective element of the cannula assembly shown in FIGS. 1 to 3.
Figure 5A:
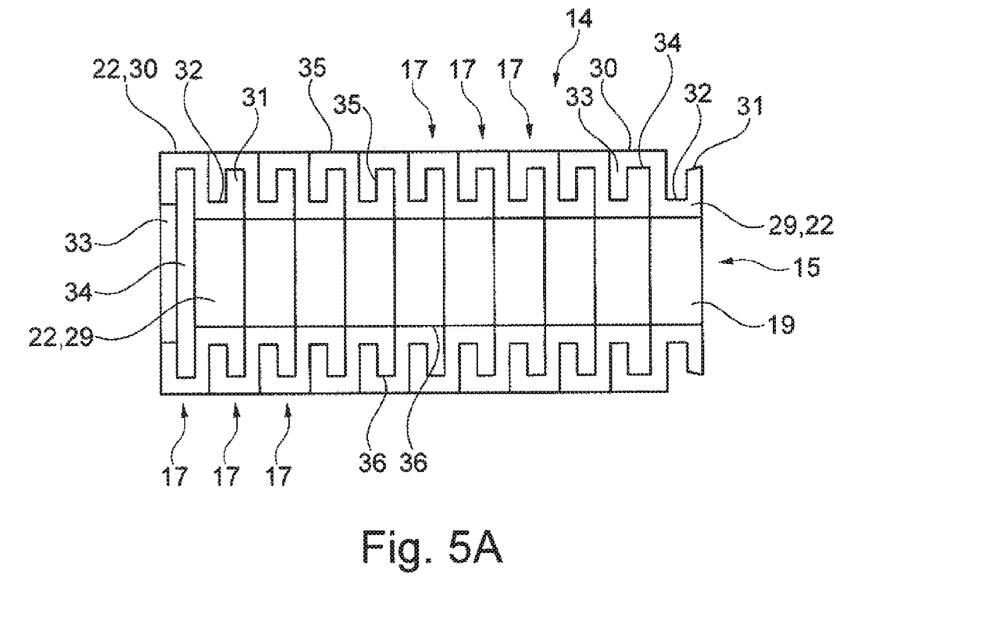
FIG. 5A shows a sectional illustration of a further example of a protective element of the cannula assembly shown in FIGS. 1 to 3 in accordance with a longitudinal section through the protective element along a central longitudinal axis.
Figure 5B:
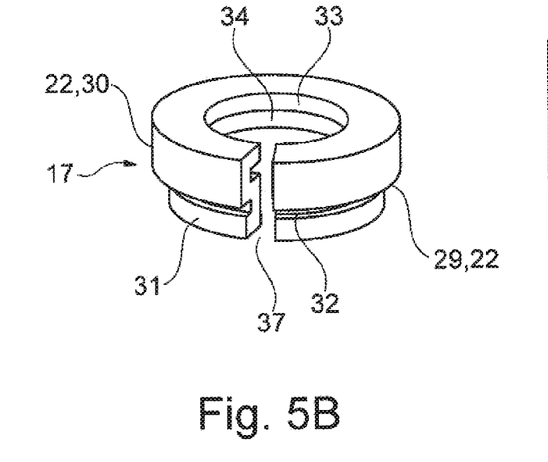
FIG. 5B shows a perspective view of an individual segment of the protective element shown in FIG. 5A.
Figure 5C:
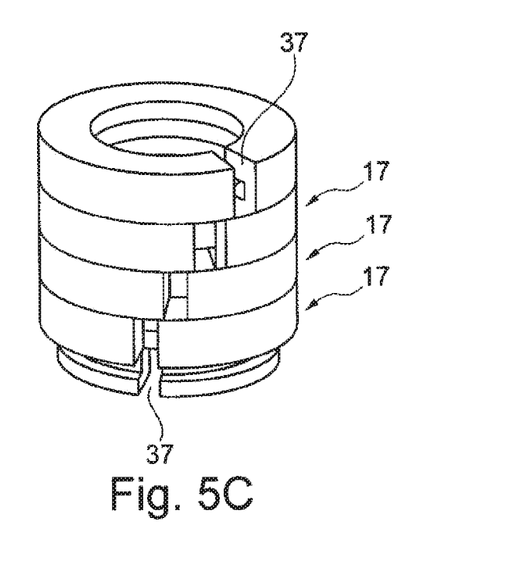
FIG. 5C shows a perspective view of a sequence of four segments, inserted one inside the other, of the protective element shown in FIGS. 5A and 5B.
Figure 6:
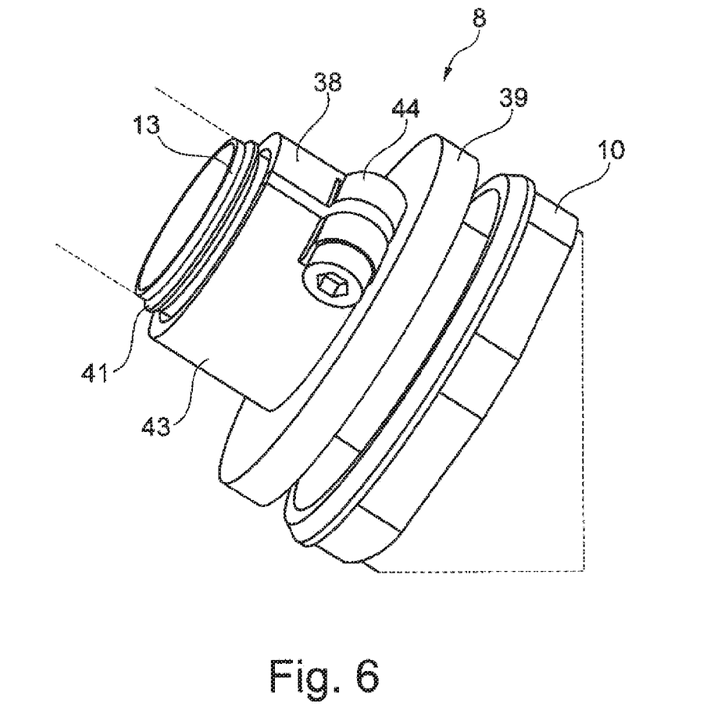
FIG. 6 shows a perspective detailed view of a front end of the cannula assembly shown in FIGS. 1 to 3.

Particular exemplary embodiments of the cannula assembly proposed here and of the blood pump assembly proposed here as well as the use thereof will be described hereinafter with reference to the schematic illustrations shown in FIGS. 1 to 7, in which:

FIG. 1 shows a side view of an example of a blood pump assembly with a cannula assembly of the type proposed here, FIG. 2 shows a side view of the cannula assembly shown in FIG. 1, FIG. 3 shows a sectional illustration of the cannula assembly shown in FIG. 2 in accordance with the longitudinal section marked in FIG. 2 and denoted by the numeral III, FIGS. 4A-4C show perspective views of an example of a protective element of the cannula assembly shown in FIGS. 1 to 3, FIG. 5A shows a sectional illustration of a further example of a protective element of the cannula assembly shown in FIGS. 1 to 3 in accordance with a longitudinal section through the protective element along a central longitudinal axis, FIG. 5B shows a perspective view of an individual segment of the protective element shown in FIG. 5A, FIG. 5C shows a perspective view of a sequence of four segments, inserted one inside the other, of the protective element shown in FIGS. 5A and 5B, FIG. 6 shows a perspective detailed view of a front end of the cannula assembly shown in FIGS. 1 to 3, and FIG. 7 shows a lateral view of a number of components of the blood pump assembly shown in FIG. 1.

In the figures and the following description, identical features or features corresponding to one another are provided in each case with the same reference signs.

FIG. 1 shows an implantable blood pump assembly 1 of the type proposed here, comprising an implantable cannula assembly 2 of the type proposed here and an implantable blood pump 3. The blood pump 3 is embodied in the present case for example as an axial pump and comprises an inlet 4 and an outlet 5. The inlet 4 is connectable to a left ventricle of a heart via an inlet manifold 6 of the blood pump 3. The outlet 5 is releasably connected to a front end 8 of the cannula assembly 2 via an outlet manifold 7 of the blood pump 3. For this purpose, the cannula assembly 2, at its front end 8, comprises a connector 9, which is embodied in this example as a snap-action connector having a plurality of flexible snap-action elements 46 (see FIGS. 3 and 7). The blood pump 3 comprises a connection part 10, which corresponds to the connector 9 and which is fastened to an axial end region 11 of the outlet manifold 2. The cannula assembly 2 can be connected via a rear end 12 for example to an aortic arch.

The cannula assembly 2 comprises a cannula 13 in the form of a graft, which for example comprises a textile carrier structure made of woven or knitted polyester fibres in the form of a corrugated tube (see also FIGS. 2 and 3). The carrier structure is sealed by means of sealing material, for example by means of beef gelatine, and is thus liquid-tight. The cannula 13 can be connected to the aortic arch or another blood vessel directly at the rear axial endpiece of the cannula or via a connection element, for example via a sewing ring (not shown).

The cannula assembly 2 additionally comprises a protective element 14 for the cannula 2, which is intended to prevent, to the greatest possible extent, the relatively soft and flexible cannula 2 from becoming kinked, compressed or damaged. The protective element 14 is a component of the cannula assembly 2 produced separately and independently of the cannula 13. As can be seen particularly clearly from FIGS. 2 and 3, the protective element 14 in its interior forms a channel 15 for the cannula 13. The cannula 13 runs in sections through this channel 15. Accordingly, the flow channel 16 delimited laterally by the cannula 13 also runs in sections within the channel 15 of the protective element 14. The channel 15 and the flow channel 16 run substantially in parallel and coaxially with one another, at least in the portions in which the flow channel 16 runs through the channel 14.

When the cannula assembly 2 is assembled, the cannula 13 is introduced in part into the channel 15 of the protective element 14, for example by pulling the cannula 13 into the channel 15 or by pushing or pulling the protective element 14 over the cannula 13. The channel 15 are sufficiently wide to enable axial displacements of the protective element 14 relative to the cannula 13. For this purpose, a diameter $D_S$ of the substantially circular cross section of the channel 15 is larger than a maximum outer diameter $D_K$ of the cannula 13 provided in the form of corrugated tube.

As can also be clearly seen in FIGS. 2 and 3, the protective element 14 comprises a plurality of segments 17, for example ten segments 17. The segments 17 are arranged next to one another in a linear sequence. Each of the segments 17 defines an axial sub-section of the channel 15 of the protective element 14. For this purpose, the segments 17 are sleeve-shaped and each have an opening 18, which openings run through the respective segments 17 fully in the direction of the sequence of the segments 17 and form the aforesaid axial sub-section of the channel 15. The above-described diameter $D_K$ corresponds therefore to the inner diameter of the segments 17, that is to say the diameter of the openings 18. A free gap 21, which can be formed at least in sections as an annular gap, is thus created between inner walls 19 of the segments 17, which in each case define the channel 15 radially and define the openings 18, and an outer surface 20 of the cannula 13.

The proposed protective element 14 additionally comprises connection elements 22 (see FIGS. 4A-C and FIGS. 5A-C) which connect the segments 17 to one another. Various specific exemplary embodiments for connection elements 22 of this kind will be described in detail further below with reference to FIGS. 4A-C and 5A-C. On account of the connection elements 22, the segments 17 and the connection elements 22 of the protective element 14 form a unit which is held together in a mechanically stable manner independently of the cannula 13 and other components.

The segments 17, similarly to the connection elements 22, are formed fully of a resiliently deformable polymer, for example silicone. The segments 17 and also the connection elements 22 for example are injection-moulded parts, that is to say have been produced by injection moulding. The segments 17 are of identical form in a mechanically unloaded state; the connection elements 22 are also of identical form in a mechanically unloaded state.

FIGS. 4A-4C show a particular exemplary embodiment for the protective element 14 of the cannula assembly 2 shown in FIGS. 1-3. The connection elements 22 of the protective element 14 are embodied in this example as cable-shaped elements 23. Each of the cable-shaped elements 23 is directly connected to each of the segments 17 and is directly fastened thereto, for example by adhesive bonding, for example by means of a silicone adhesive. The cable-shaped elements 23 extend each case in an axial direction along the arrangement of the segments 17, that is to say in particular along the channel 15 of the protective element 14. The cable-shaped elements 23 are formed in a tube-like manner, but in principle could also be embodied without an inner cavity, that is to say for example in the form of a wire. Alternatively, a strip-shaped element can be used, which for example has a width equal to a segment circumference of 90° of the segment. Alternatively, a tubular, for example perforated element can be provided, which surrounds the segments in a tube-like manner. Here, the perforation provides a possibility for ensuring the rotatability.

The cable-shaped elements 23 are arranged in a manner distanced from one another around the segments 14 in respect of an azimuthal circumferential direction. Here, the cable-shaped elements 23 are distributed uniformly over the circumference of the segments 17. In the present example of three cable-shaped elements 23, the azimuthal distances therebetween are approximately 120°.

Each of the segments 17 has a radially outwardly directed protrusion 24. The cable-shaped elements 23 are supported and fastened at these protrusions 24, for example by gluing. The protrusions 24 are embodied as annular widened portions of the respective segments 17 and have receptacles 25 in the form of radial indentations, through each of which an axial sub-section 26 of a cable-shaped element 23 passes. An axial extent of each of the protrusions 24 is smaller than an axial extent of the corresponding segment 17, such that the cable-shaped elements 23 between the protrusions 24 are distanced in the radial direction from the segments 17, that is to say are self-supporting. The cable-shaped elements 23 in these regions can thus be severed relatively easily by means of a hand-held cutting instrument 27, for example by means of a scalpel, without damaging the corresponding segment 17 or even the cannula 13 (see FIG. 4B).

As is shown in FIG. 4C, once all three cable-shaped elements 23 between two adjacent segments 17 have been severed, the two separate segments 17 can be pulled apart from one another. In this way, segments 17 not required can be removed from the cannula assembly 2, for example by being pulled over an end of the cannula 13. The cannula 13, previously or subsequently, can likewise be shortened by means of a suitable cutting instrument.

In addition, it is possible to rotate segments 17 arranged next to one another in the sequence relative to one another through 5° about a longitudinal axis of the channel 15, without at the same time damaging the cable-shaped elements 23, the segments 17, or even the graft.

FIGS. 5A-5C show a further particular exemplary embodiment for the protective element 14 of the cannula assembly 2 shown in FIGS. 1-3. The connection elements 22 of the protective element 14 are in this example integrated in axial end regions of the segments 17. Each of the segments 17 has a first axial end region 29 and a second axial end region 30, wherein the first axial end regions 29 are formed in a manner complementary to the second axial end regions 30. The first and the second axial end regions 29, 30 of each two segments 17 next to one another in the sequence overlap axially and are in mutual engagement. This engagement creates a mechanical connection between the segments 17. Since, in this example, the segments 17 consist completely of silicone, the segments 17 as a whole and in particular also in their axial end regions 29, 30 are elastically deformable. The form-fitting connections between adjacent segments can therefore be produced and cancelled particularly easily by manually axially pushing together or pulling apart the segments 17, respectively.

The first axial end region 29 of each segment 17 has a first rib 31 and a first groove 32, wherein the first rib 31 and the first groove 32 are arranged on an outer side 35 (that is to say on an outer surface) of the particular segment 17 facing away from the channel 15 radially. The second axial end region 30 of each segment 17 has a second rib 33, which is formed in a manner complementary to the first groove 32, and a second groove 34, which is formed in a manner complementary to the first rib 31, wherein the second rib 33 and the second groove 34 are arranged on an inner side 36 (that is to say on an inner surface) of the particular segment 17 facing the channel 15 radially. The first rib 31 axially borders the first groove 32. Accordingly, the second rib 33 axially borders the second groove 34. With mutual engagement of the first axial end region 29 and the second axial end region of two segments 17 next to one another in the sequence, the first and second ribs 31, 33 engage one another from behind axially, wherein the first rib 31 dips into the second groove 34 and the second rib 33 dips into the first groove 34. The first ribs 31 and the second grooves 34 are directed radially outwardly. The second ribs 33 and the first grooves 32 are directed radially inwardly. The first and second ribs 31, 33 and the first and second grooves 32, 34 run fully around the respective segment in a circumferential direction (azimuthally). It is possible to rotate segments 17 which are next to one another in the sequence relative to one another through 360° about a longitudinal axis of the channel 15 without detaching the segments 17 from one another or damaging the graft.

As can be seen in FIGS. 5B and 5C, the segments 17 each have a slot 37 which extends in the axial direction over the total axial length of the corresponding segment 17 and in the radial direction from the outer side 35 (outer surface) of the particular segment 17 to the inner side 36 (inner surface), that is to say as far as the channel 15. The slot 37 of each segment 17 can be manually widened until the segment 17, if it has been previously separated from the adjacent segments 17, can be pulled down from the cannula 13 in a lateral, non-axial direction. The segments shown in FIGS. 4A-4C can each have a slot 37 of this kind.

As is visible for example from FIGS. 3 and 6, the cannula 13 at the front end 8 of the cannula assembly 2 has a connection element 38, which is designed to produce a fluid-tight connection between the cannula 13 and a further conduit element 39 for the liquid to be conveyed. The conduit element 39 is in this example a pipe element (olive) made of titanium, which is inserted via a first end 40 (pipe socket) into a front axial end region 41 of the cannula 2. A second end 42 (pipe socket) of the conduit element 39 is inserted into the axial end region 11 of the outlet manifold 7 manufactured from silicone.

The connection element 38 is embodied in the form of a metal clamp which surrounds the axial end region 41 of the cannula 13. The clamp can be clamped by means of a clamping bolt 43 and a corresponding threaded element 44 so as to press the axial end region 41 of the cannula radially inwardly onto the first end 40 of the conduit element 39 and thus produce a fluid-tight clamping connection between the cannula 2 and the conduit element 39.

Figure 7:
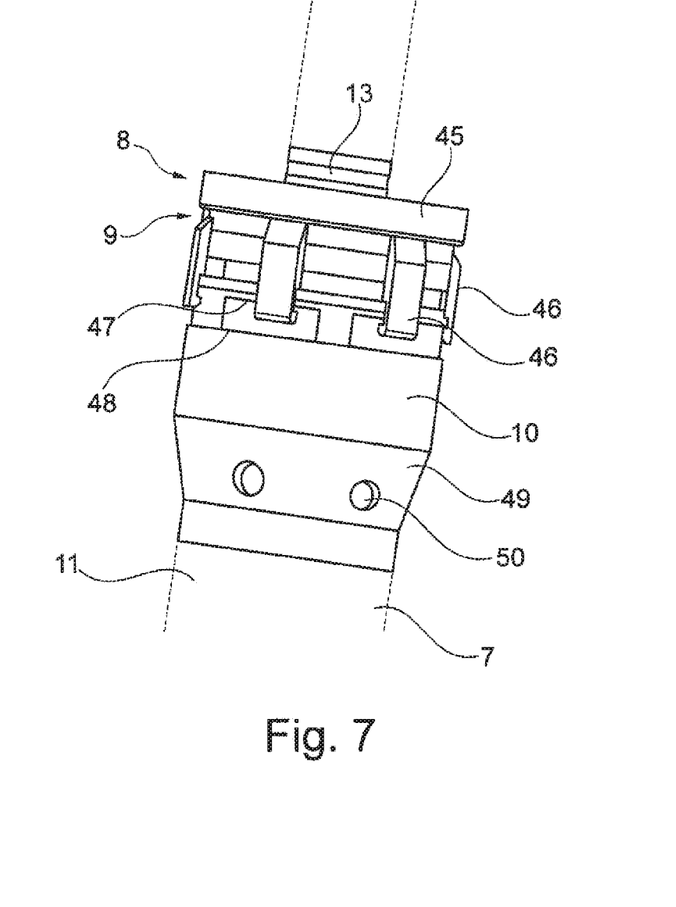
FIG. 7 shows a lateral view of a number of components of the blood pump assembly shown in FIG. 1.

As can be best seen in FIGS. 3 and 7, the connector 9 at the front end 8 of the cannula assembly 2 is fastened to a foremost segment 17 of the protective element 14. The connector 9 embodied as a snap-action connector comprises a claw ring 46, which has a plurality of flexible snap-action elements 46 embodied as claws. The claw ring 45 can be embodied for example in the manner of the claw ring described in publication WO 2004/001272 A1. The claw ring 45 is preferably mounted rotatably and/or (axially) displaceably on a foremost segment 17 of the protective element 14. The connector 9 additionally comprises a stop ring 54. The claw ring 46 in the latched state presses with an axial contact force against the stop ring 54, which transfers the axial contact force onto the foremost segment 17. For example, an axial end face of the foremost segment 17 is in this way pressed for example onto a bordering axial end face of the conduit element 39 or of the connection part.

The corresponding connection part 10 has holding surfaces 47 for producing a releasable latched connection between the holding surfaces 47 and the snap-action elements 46 (claws). The connection part 10 comprises a detent ring 48, on which the holding surfaces are formed as detent ring holding surfaces. The detent ring 48 and/or the holding surfaces 48 can be embodied for example in the manner of the detent ring described in publication WO 2004/001272 A1 or the detent ring holding surfaces described there.

The connection part 10 is an adapter element which is manufactured wholly or at least partially from titanium and which is fixedly connected to the outlet manifold 7 of the blood pump 3 by means of an adhesive. For example, one possible adhesive is a silicone adhesive. The adapter element can have a sleeve-shaped region 49, which fully encircles the axial end region 11 of the outlet manifold 7. In the shown example the detent ring 48 is integrated in the connection part 10 and axially borders the sleeve-shaped region, that is to say is embodied as an axial end region of the connection part 10. A protective sleeve 55 forms an outer sleeve around the claw ring 46 and the detent ring 48.

The sleeve-shaped region 49 has radially extending openings 50. Starting from the axial end region 11, fastening elements 51 run through the openings 50 and connect the adapter element to the outlet manifold 11. The fastening elements 51 are made of the above-mentioned adhesive and are connected in an integrally bonded manner (adhesively bonded) via their foot ends 52 to the axial end region 11 of the outlet manifold 7. Head ends 53 of the fastening elements 51 protrude from the openings 51 and in so doing protrude both radially outwardly and laterally beyond the outer edges of the openings 51. Since the head ends 53 are wider than the openings 50, the fastening elements 51 cause a form-fitting connection between the outlet manifold 7 and the adapter element, similarly to a rivet connection.

To clarify the use of and to hereby provide notice to the public, the phrases "at least one of <A>, <B>, . . . and <N>" or "at least one of <A>, <B>, . . . <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed. Unless otherwise indicated or the context suggests otherwise, as used herein, "a" or "an" means "at least one" or "one or more."

While various embodiments have been described, it will be apparent to those of ordinary skill in the art that many more embodiments and implementations are possible. Accordingly, the embodiments described herein are examples, not the only possible embodiments and implementations.

LIST OF REFERENCE SIGNS 1 blood pump assembly
2 cannula assembly
3 blood pump
4 inlet
5 outlet
6 inlet manifold
7 outlet manifold
8 front end
9 connector
10 connection part
11 axial end region
12 rear end
13 cannula
14 protective element
15 channel
16 flow channel
17 segment
18 opening
19 inner wall
20 outer surface
21 intermediate gap
22 connection element
23 cable-shaped element
24 protrusion
25 receptacles
26 sub-section
27 cutting instrument
28 first axial end region
29 second axial end region
30 first rib
31 first groove
32 second rib
33 second groove
34 outer side
35 inner side
36 slot
37 connection element
38 conduit element
39 first end
40 axial end region
41 second end
42 clamping bolt
43 threaded element
44 claw ring
45 snap-action element, claw
46 holding surface 47 detent ring
48 region
49 opening
50 fastening element
51 foot end
52 head end
53 stop ring
54 protective sleeve

The invention claimed is:

1. A cannula assembly comprising:
a cannula for forming a flow channel for bodily fluids; and
a protective element for the cannula, wherein the protective element defines a channel for the cannula, wherein the cannula runs through the channel of the protective element at least in sections, wherein the protective element comprises a plurality of segments, wherein the segments are arranged next to one another in a sequence and wherein each segment of the plurality of segments defines a subsection of the channel of the protective element, wherein the segments are connected to one another in such a way that the segments are rotatable relative to one another about a longitudinal axis of the channel, wherein at least one segment of the plurality of segments has a slot which extends in an axial direction over an axial total length of the respective segments and in a radial direction from an outer side of the respective segments facing away from the channel to an inner side of the segments facing the channel.

2. The cannula assembly according to claim 1, wherein the cannula is a graft that has a textile carrier structure.

3. The cannula assembly according to claim 1, wherein the segments are connected to one another in such a way that the segments arranged next to one another in the sequence are rotatable relative to one another through at least 3° or through at least 5° about a longitudinal axis of the channel.

4. The cannula assembly according to claim 1, wherein an inner diameter (DS) of the segments is larger than an outer diameter (DK) of the cannula.

5. The cannula assembly according to claim 1, wherein the segments are formed wholly or at least partially from a resiliently deformable polymer.

6. The cannula assembly according to claim 1, wherein the segments comprise injection-moulded parts.

7. The cannula assembly according to claim 1, wherein the segments are of identical form when undeformed.

8. The cannula assembly according to claim 1, wherein the protective element comprises at least one cable-shaped element, wherein the at least one cable-shaped element is directly connected to at least two segments of the plurality of segments.

9. The cannula assembly according to claim 8, wherein the at least one cable-shaped element comprises at least two cable-shaped elements of this kind, wherein the cable-shaped elements are arranged distanced from one another in a circumferential direction around the protective element.

10. The cannula assembly according to claim 8, wherein the segments have radially outwardly directed protrusions, at which the at least one cable-shaped element is supported and/or fastened, wherein the at least one cable-shaped element runs in a freely-supporting manner wholly or at least in sections between the radially outwardly directed protrusions.

11. The cannula assembly according to claim 1, wherein each of the segments has a first axial end region and a second axial end region, wherein the first axial end regions of the segments are formed in a manner complementary to the second axial end regions of the segments, wherein the first and second axial end regions of the segments that are arranged next to one another in the sequence overlap axially and are in mutual engagement.

12. The cannula assembly according to claim 11, wherein the first axial end region of each segment has a first rib and a first groove, wherein the first rib and the first groove are arranged on an outer side of at least one segment of the plurality of segments facing away from the channel, wherein the second axial end region of each segment of the plurality of segments has a second rib, which is formed in a manner complementary to the first groove, and a second groove, which is formed in a manner complementary to the first rib, wherein the second rib and the second groove are arranged on an inner side of at least one segment of the plurality of segments facing the channel.

13. The cannula assembly according to claim 12, wherein the first groove and/or the second groove is furrow-shaped.

14. The cannula assembly according to claim 11, wherein the segments are of identical form when undeformed.

15. The cannula assembly according to claim 1, wherein the cannula has a connection element in the form of a clamp which surrounds an axial end region of the cannula.

16. A cannula assembly comprising:
a cannula for forming a flow channel for bodily fluids; and
a protective element for the cannula, wherein the protective element defines a channel for the cannula, wherein the cannula runs through the channel of the protective element at least in sections, wherein the protective element comprises a plurality of segments, wherein the segments are arranged next to one another in a sequence and wherein each segment defines a subsection of the channel of the protective element, wherein the segments are connected to one another in a form-fitting manner, wherein at least one segment of the plurality of segments has a slot which extends in an axial direction over an axial total length of the respective segments and in a radial direction from an outer side of the respective segments facing away from the channel to an inner side of the segments facing the channel.

17. A cannula assembly comprising:
a cannula for forming a flow channel for bodily fluids; and
a protective element for the cannula, wherein the protective element defines a channel for the cannula, wherein the cannula runs through the channel of the protective element at least in sections, wherein the protective element comprises a plurality of segments, wherein the segments are arranged next to one another in a sequence and wherein each segment defines a subsection of the channel of the protective element, wherein the protective element comprises connection elements which connect the segments to one another, wherein the connection elements are connected to the segments in an integrally bonded manner, wherein at least one segment of the plurality of segments has a slot which extends in an axial direction over an axial total length of the respective segments and in a radial direction from an outer side of the respective segments facing away from the channel to an inner side of the segments facing the channel.

18. The cannula assembly according to claim 17, wherein the segments are of identical form when undeformed.

19. A blood pump assembly comprising the cannula assembly according to claim 17, and comprising a blood pump, wherein the cannula assembly has a connector at a front end of the cannula assembly, wherein the blood pump has a connection part corresponding to the connector for producing a releasable connection between the cannula assembly and the blood pump.

20. The blood pump assembly according to claim 19, wherein the connector is arranged on a foremost segment of the protective element.

21. The blood pump assembly according to claim 19, wherein the connector is arranged rotatably and/or displaceably on a foremost segment of the protective element.

22. The blood pump assembly according to claim 19, wherein the connector is a snap-action connector having at least one flexible snap-action element, and wherein the connection part of the blood pump has at least one holding surface for producing a releasable detent connection between the at least one holding surface and the at least one flexible snap-action element.

23. The blood pump assembly according to claim 19, wherein the connection part of the blood pump is an adapter element which is fixedly connected to a conduit element of the blood pump.

24. The blood pump assembly according to claim 23, wherein the adapter element has a region which at least partially surrounds an end of the conduit element, wherein the region has substantially radially extending openings, wherein fastening elements which connect the adapter element to the conduit element run through the openings starting from the conduit element.

25. The blood pump assembly according to claim 23, wherein the adapter element is made partially or wholly from a metal material.

26. A method of shortening a protective element for a cannula, the method comprising:

separating at least two segments of the protective element, wherein the protective element defines a channel for the cannula, wherein the cannula runs through the channel of the protective element at least in sections, wherein the at least two segments are arranged next to one another in a sequence, wherein each segment of the at least two segments defines a subsection of the channel of the protective element, wherein the at least two segments are connected to one another in such a way that the segments are rotatable relative to one another about a longitudinal axis of the channel, and wherein at least one segment of the at least two segments has a slot which extends in an axial direction over an axial total length of the respective segments and in a radial direction from an outer side of the respective segments facing away from the channel to an inner side of the segments facing the channel, wherein the separating comprises:

severing at least one connection element from a plurality of connection elements of the protective element, wherein the at least one connection element connects the at least two segments; and/or pulling the at least two segments away from one another manually until an existing mutual engagement between the connection elements has been cancelled.

* * * * *